United States Patent
Alali et al.

(10) Patent No.: US 12,181,628 B2
(45) Date of Patent: *Dec. 31, 2024

(54) METHOD AND APPARATUS FOR CONTINUOUSLY CHECKING CASING CEMENT QUALITY

(71) Applicant: SAUDI ARABIAN OIL COMPANY, Dhahran (SA)

(72) Inventors: Ammar Alali, Dhahran (SA); Husain Nassir, Safwa (SA); Ezzedeen Alfataeirge, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 71 days.

This patent is subject to a terminal disclaimer.

(21) Appl. No.: 18/064,818

(22) Filed: Dec. 12, 2022

(65) Prior Publication Data

US 2023/0115721 A1    Apr. 13, 2023

Related U.S. Application Data

(62) Division of application No. 16/925,775, filed on Jul. 10, 2020, now Pat. No. 11,525,939.

(51) Int. Cl.
*G01V 8/16* (2006.01)
*E21B 47/005* (2012.01)
(Continued)

(52) U.S. Cl.
CPC .............. *G01V 8/16* (2013.01); *E21B 47/005* (2020.05); *E21B 47/07* (2020.05); *G01K 11/32* (2013.01); *G01L 1/247* (2013.01); *G01N 33/383* (2013.01)

(58) Field of Classification Search
CPC ........ E21B 47/005; E21B 47/07; G01K 11/32; G01L 1/247; G01V 3/16
See application file for complete search history.

(56) References Cited

U.S. PATENT DOCUMENTS 8,505,625 B2 * 8/2013 Ravi ..................... E21B 33/14
                                                                166/250.14
9,546,548 B2 * 1/2017 Hartog .................... G01V 1/44
(Continued)

FOREIGN PATENT DOCUMENTS

GB          2522061 A  * 7/2015 ............ E21B 47/00

OTHER PUBLICATIONS

Raab et al. "Real-Time Well-Integrity Monitoring Using Fiber-Optic Distributed Acoustic Sensing" Society of Petroleum Engineers Journal, pp. 1997-2009, SPE 195678 (Year: 2019).*

*Primary Examiner* — John Fitzgerald
(74) *Attorney, Agent, or Firm* — Osha Bergman Watanabe & Burton LLP

(57) ABSTRACT

A system for monitoring downhole cement quality in a cased well includes an active acoustic source that generates acoustic waves, a distributed acoustic sensor, and a controller. The distributed acoustic sensor includes an optical fiber disposed on an outer surface of a casing of the cased well; a pulsed laser coupled to the optical fiber and that transmits pulses of laser light along the optical fiber; a sensor that detects light that is backscattered and reflected by the optical fiber; and a processor that controls the pulsed laser, receives signals from the sensor, and converts the signals into acoustic information. The controller receives the acoustic information from the processor and identifies well integrity loss.

2 Claims, 8 Drawing Sheets

(51) Int. Cl.
  *E21B 47/07*    (2012.01)
  *G01K 11/32*    (2021.01)
  *G01L 1/24*     (2006.01)
  *G01N 33/38*    (2006.01)

(56) References Cited

U.S. PATENT DOCUMENTS

| | | | |
|---|---|---|---|
| 9,828,849 B2* | 11/2017 | Godfrey | E21B 47/10 |
| 10,890,064 B2* | 1/2021 | Reinsch | E21B 47/16 |
| 11,525,939 B2* | 12/2022 | Alali | G01V 8/16 |
| 11,650,346 B2* | 5/2023 | Chang | E21B 47/107 |
| | | | 73/152.16 |
| 11,661,838 B2* | 5/2023 | Singh | G01V 1/40 |
| | | | 702/6 |
| 2009/0168597 A1* | 7/2009 | Wu | E21B 47/005 |
| | | | 367/33 |
| 2012/0205103 A1* | 8/2012 | Ravi | E21B 33/14 |
| | | | 166/285 |
| 2014/0174726 A1* | 6/2014 | Harrigan | E21B 31/005 |
| | | | 166/177.2 |
| 2014/0216151 A1* | 8/2014 | Godfrey | G01F 1/704 |
| | | | 73/152.32 |
| 2017/0075029 A1* | 3/2017 | Cuny | G01V 1/52 |
| 2017/0090054 A1* | 3/2017 | Willis | G01V 1/42 |
| 2018/0238167 A1* | 8/2018 | Ravi | G01V 1/226 |
| 2021/0199832 A1* | 7/2021 | Wu | E21B 47/135 |

\* cited by examiner

METHOD AND APPARATUS FOR CONTINUOUSLY CHECKING CASING CEMENT QUALITY

CROSS-REFERENCE TO RELATED APPLICATIONS

This Application is a Division of application Ser. No. 16/925,775 filed on Jul. 10, 2020. The entire contents of these applications are incorporated herein by reference in their entirety.

BACKGROUND

Extraction of oil, gas, and water from a subterranean formation via an oil and gas well can involve significant risks. Well integrity, defined as application of technical, operational and organizational solutions to reduce risk of uncontrolled release of formation fluids (i.e., liquids and gases), is critical in the petroleum industry and needs to be maintained throughout the entire life cycle of the well. Well integrity refers to maintaining full control of fluids within a well at all times in order to prevent unintended fluid movement or loss of fluid containment to the surrounding environment. The uncontrolled escape of fluids from the formation to other subterranean formations and/or the earth's surface results in unplanned Sustained Annulus Pressure (SAP) or Sustained Casing Pressure (SCP). This uncontrolled pressure is also referred to as Casing-Casing Annulus (CCA) pressure buildup if it is built up between two casing strings. Alternatively, it is called Tubing-Casing Annulus (TCA) pressure buildup if it is between the production tubing and casing. Unplanned TCA pressure may be a result of a leak in a completion component or liner top packer. Unplanned CCA pressure may be due to a cementation failure. Many factors may contribute to damaged cement, resulting in compromised well integrity. Sustained CCA or TCA pressure is a common well integrity management challenge. These challenges often result in wells being closed pending workover.

To control CCA pressure, a proper "cement job" is the main element that protects the wellbore components and provides isolation from the formation and its fluids (i.e., liquids or gases). A proper cement job ensures the presence of competent barriers to prevent fluid bypass to the earth's surface or another subterranean formation. Many cement strategies exist to enhance the shear bond and mechanical properties to prevent cement cracking, which may eventually lead to CCA buildup. In addition, proper cement placement between the well casing and formation is essential to support the casing, to prevent fluids from leaking to the surface, and to isolate producing zones, i.e., zones that produce hydrocarbon fluid, from the water-bearing zones.

Nonetheless, due to different factors, applied cement may lose its casing-formation bond and/or get damaged, developing what is known as external integrity failure, i.e., geofluids (i.e., liquids or gases) migration through a damaged cement sheath into the CCA. Remediation of external integrity failure is difficult. Industry recommended practices recognize the difference between casing pressures that are thermally induced, operator induced, or initiated by an internal integrity failure process (i.e., those resulting from reverse migration).

This damaged zone in the cement usually starts in a small patch and can take time (for example, weeks or months) before the damaged zone develops and propagates to the surface causing the uncontrolled pressure buildup and/or other problems like fluid bypass between different zones.

Proper monitoring of the cement quality and integrity, quantitatively and continuously, is vital in detecting any cracks or problems in the cement at an early stage and control the cracks or problems and stop their development before the failure reaches a more problematic stage.

SUMMARY

In general, in one aspect, embodiments relate to a system for monitoring downhole cement quality in a cased well. The system may include an active acoustic source that generates acoustic waves; a distributed acoustic sensor; and a controller. The distributed acoustic sensor may include an optical fiber disposed on an outer surface of a casing of the cased well; a pulsed laser coupled to the optical fiber and that transmits pulses of laser light along the optical fiber; a sensor that detects light that is backscattered and reflected by the optical fiber; and a processor that controls the pulsed laser, receives signals from the sensor, and converts the signals into acoustic information. The controller may receive the acoustic information from the processor and identifies well integrity loss.

In general, in one aspect, embodiments relate to a method of monitoring downhole cement quality in a cased well that includes transmitting acoustic waves into the earth from an active acoustic source; detecting acoustic waves transmitted by the active acoustic source using a distributed acoustic sensing system, where the distributed acoustic sensing system includes: an optical fiber having inhomogeneities that reflect and backscatter light; a pulsed laser that transmits pulsed laser light along the optical fiber, wherein a portion of the pulsed laser light is reflected and backscattered; and a detector that detects the reflected and backscattered laser light; analyzing the detected light; and identifying loss of well integrity based on the detected light.

In general, in one aspect, embodiments relate to a method of monitoring downhole cement quality in a cased well that includes: passively detecting acoustic waves using a distributed acoustic sensing system, where the distributed acoustic sensing system includes: an optical fiber having inhomogeneities that reflect and backscatter light; a pulsed laser that transmits pulsed laser light along the optical fiber, wherein a portion of the pulsed laser light is reflected and backscattered; and a detector that detects the reflected and backscattered laser light; analyzing the detected light; and identifying loss of well integrity based on the detected light.

The foregoing general description and the following detailed description are exemplary and are intended to provide an overview or framework for understanding the nature of the invention as it is claimed. The accompanying drawings are included to provide further understanding of the invention and are incorporated in and constitute a part of the specification. The drawings illustrate various embodiments of this disclosure and together with the description serve to explain the principles and operation of the disclosure.

Other aspects of the disclosure will be apparent from the following description and the appended claims.

BRIEF DESCRIPTION OF DRAWINGS

The following is a description of the figures in the accompanying drawings. In the drawings, identical reference numbers identify similar elements or acts. The sizes and relative positions of elements in the drawings are not necessarily drawn to scale. For example, the shapes of various elements and angles are not necessarily drawn to scale, and some of these elements may be arbitrarily enlarged and positioned to improve drawing legibility. Further, the particular shapes of the elements as drawn are not necessarily intended to convey any information regarding the actual shape of the particular elements and have been solely selected for ease of recognition in the drawing.

DETAILED DESCRIPTION

Figure 1:
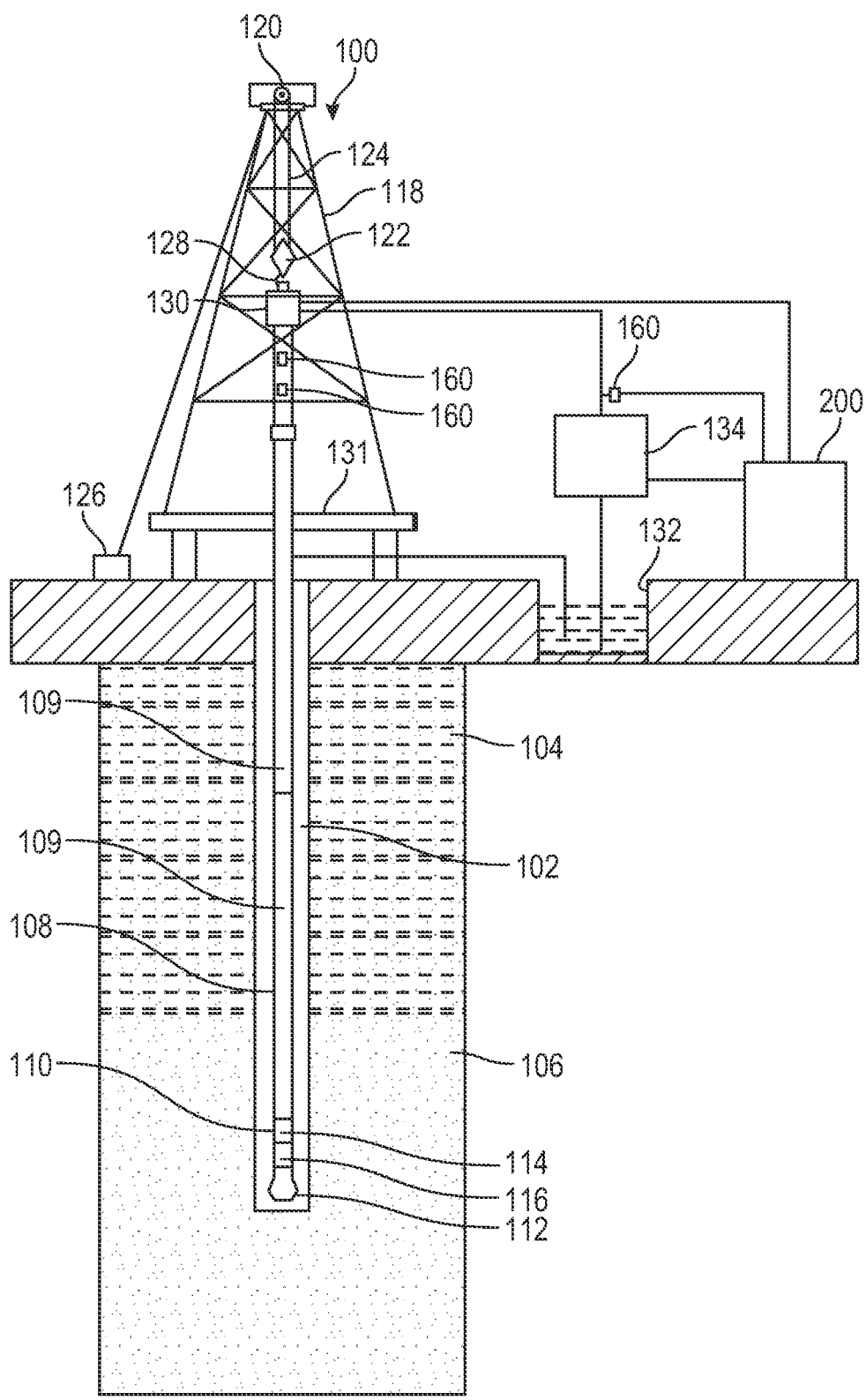
FIG. 1 is a schematic diagram of an exemplary well site in accordance with one or more embodiments.

In the following detailed description, certain specific details are set forth in order to provide a thorough understanding of various disclosed implementations and embodiments. However, one skilled in the relevant art will recognize that implementations and embodiments may be practiced without one or more of these specific details, or with other methods, components, materials, and so forth. In other instances, well known features or processes associated with hydrocarbon production systems have not been shown or described in detail to avoid unnecessarily obscuring descriptions of the implementations and embodiments. For the sake of continuity, and in the interest of conciseness, same or similar reference characters may be used for same or similar objects in multiple figures.

One or more embodiments disclosed herein may provide a continuous cement quality check for purposes of maintaining well integrity. Embodiments disclosed herein use acoustic waves as a detection principle. In one or more embodiments, a permanent behind-the-casing optical fiber cable (for Distributed Acoustic Sensing, or DAS) is employed as a receiver, and a permanent active acoustic source installed directly on the casing top flange or a suitable distance away (offset) from the wellbore. The maximum offset is proportional to the well target depth. The angle of incidence of the acoustic wave must be within 5 degrees of vertical incidence. The DAS may be performed with a single optical fiber, though the installation of a DAS system may be done using an armored cable that may house a plurality of fibers in an optical fiber bundle. The acoustic source may generate an acoustic wave with a frequency range that is pre-determined based on the depth of the well.

The earth naturally filters high frequencies. The frequency of the source is proportional to the resolution such that the highest resolution is one quarter of the wavelength, where $f=v/\lambda$ with f being the frequency, v the formation velocity, and $\lambda$ the wavelength). With deeper wells (e.g., thousands of meters measured depth), a lower frequency (0-200 Hz) may be needed for deeper penetration of the source field. In shallower wells (hundreds of meters measured depth), higher frequencies may be used (up to 500 Hz). The acoustic wave propagates from the acoustic source and may pass through the formation, cement and casing to the behind-casing fiber optics.

In one or more embodiments, the acquisition system may be operated in a time-lapse mode, acquiring data on a routine, periodic basis (for example, daily or weekly). The time-lapse approach may be used to identify changes in the physical states of the casing cement, such as cement cracks, cement-casing bond failure, or other problems in the cement that may be detected in the early stages, within oil-gas reservoirs.

In one or more embodiments, the overlapped acoustic data, i.e., acoustic data acquired over time in the time-lapse approach, may help detect any newly formed acoustic signatures of fractures and/or wearing cement as a function of varying acoustic wave velocity (delay) and/or acoustic wave amplitude. The time-lapse analysis may include measurements of repeatability and normalized root mean square (NMRS) amplitude analysis to ensure that any observed changes are due to cement degradation and not to other factors such as acoustic acquisition or processing.

Processed acoustic data of acoustic waves that have passed through cement fractures and/or a loose casing-cement bond may have one of three potential signatures of fractures and/or wearing cement. First, the acoustic data may have a pronounced high amplitude data vibration and anomalies in the acoustic wave velocity, usually generated as the casing vibrates differently in parts associated with the poor cement conditions than under good cement conditions. Second, the acoustic data may display shear-wave splitting induced by the cement fractures. Shear-wave splitting may occur in anisotropic media where the wave velocity of two orthogonal components of a shear wave propagate at different rates through the medium. Third, the acoustic data may show increased slowness in the acoustic wave as a result of fluids filling the fractures. Slowness is the reciprocal of velocity and has dimensions of time per length. The increased slowness may be seen as an increased phase delay in the fiber perturbed by the acoustic field.

One or more embodiments disclosed herein may allow monitoring the quality of cement in a wellbore without interfering with the production of hydrocarbon fluids, over more extended durations of time than conventional methods, remotely (including wireless communication of data), and detection of the location and time of a problem in real-time, as the problem evolves. Embodiments to monitor the cement continuously as disclosed herein may be non-invasive and may eliminate the need for a workover rig to identify the location where a problem originated.

In one or more embodiments, the installation of a fiber-optic cable behind casing may enable other methods of CCA evaluation via Distributed Temperature Sensing (DTS). DTS passively measures the temperature variation in the thermal gradient along the fiber. DTS data may be used to indicate flow inside and behind casing. This thermal data may be used to detect fractures behind casing that allow flow of hydrocarbons to the surface or across different geological formations. Thus, DTS may be incorporated into one or more embodiments of the present invention for monitoring downhole cement quality.

In one or more embodiments, passive monitoring of DAS amplitudes when shutting in the well may also allow for evaluation of CCA and leak detection. Passive monitoring does not require an active acoustic source but detects acoustic waves generated by other sources such as a leak in the cement, seismic events, well drilling, and the like. A borehole that has no CCA issue may exhibit low DAS amplitudes with depth. However the presence of a leak may be indicated by high DAS amplitudes emitted from the depth of the leak source.

Thus, the installation of optical fiber behind casing allows for multiple methods of CCA evaluation.

In this disclosure, terms well, oil well, gas well, oil and gas well, and like terms may be used interchangeably without narrowing the type of well unless specifically stated.

Regarding directions of a coordinate system, the axial direction may be a direction parallel to an axis of rotation. In a well, the axial direction may be the direction parallel to the wellbore and may be local. That is, if the wellbore changes direction along its length, one may still refer to an axial direction at any point along the wellbore as being tangential to the direction of the wellbore at that location. The radial direction is perpendicular to the axial direction and points along a radius away from the axis. The azimuthal direction is perpendicular to the axial and the radial directions.

A fluid is a material that is capable of flowing. Thus, both liquids and gases are fluids. In oil and gas wells, oil, gas, and water are examples of fluids that may be encountered.

In the present disclosure, the term "behind casing" refers to a position radially outside the outer surface of the casing.

FIG. 1 illustrates an exemplary well site 100. In general, well sites may be configured in a myriad of ways. Therefore, well site 100 is not intended to be limiting with respect to the particular configuration of the drilling equipment. Well site 100 is depicted as being on land. In other examples, well site 100 may be offshore, and drilling may be carried out with or without use of a marine riser. A drilling operation at well site 100 may include drilling a wellbore 102 into a subsurface including various formations, such as formations 104, 106. For the purpose of drilling a new section of wellbore 102, a drill string 108 is suspended within wellbore 102. Drill string 108 may include one or more drill pipes 109 connected to form conduit and a bottom hole assembly (BHA) 110 disposed at the distal end of the conduit. The BHA 110 may include a drill bit 112 to cut into the subsurface rock. The BHA 110 may include measurement tools, such as a measurement-while-drilling (MWD) tool 114 and logging-while-drilling (LWD) tool 116. Measurement tools 114, 116 may include sensors and hardware to measure downhole drilling parameters, and these measurements may be transmitted to the surface using any suitable telemetry system known in the art. The BHA 110 and drill string 108 may include other drilling tools known in the art but not specifically shown.

Drill string 108 may be suspended in wellbore 102 by a derrick 118. A crown block 120 may be mounted at the top of derrick 118, and a traveling block 122 may hang down from crown block 120 by means of a cable or drilling line 124. One end of cable 124 may be connected to a drawworks 126, which is a reeling device that can be used to adjust the length of cable 124 so that traveling block 122 moves up or down derrick 118. Traveling block 122 may include a hook 128 on which a top drive 130 is supported. Top drive 130 is coupled to the top of drill string 108 and is operable to rotate drill string 108. Alternatively, drill string 108 may be rotated by means of a rotary table (not shown) on the drilling floor 131. Drilling fluid (commonly called mud) may be stored in a pit (mud pit) 132, and at least one pump 134 may pump the mud from pit 132 into drill string 108. The mud may flow into drill string 108 through appropriate flow paths in top drive 130 (or a rotary swivel if a rotary table is used instead of a top drive to rotate drill string 108).

In one implementation, a system 200 may be disposed at or communicate with well site 100. System 200 may control at least a portion of a drilling operation at well site 100 by providing controls to various components of the drilling operation. In one or more embodiments, system 200 may receive data from one or more sensors 160 arranged to measure controllable parameters of the drilling operation. As a non-limiting example, sensors 160 may be arranged to measure WOB (weight on bit), RPM (drill string rotational speed), GPM (flow rate of the mud pumps), and ROP (rate of penetration of the drilling operation). Sensors 160 may be positioned to measure parameter(s) related to rotation of drill string 108, parameter(s) related to travel of the traveling block 122, which may be used to determine ROP of the drilling operation, and parameter(s) related to flow rate of pump 134. For illustration purposes, sensors 160 are shown on drill string 108 and proximate mud pump 134. The illustrated locations of sensors 160 are not intended to be limiting, and sensors 160 could be disposed wherever drilling parameters need to be measured. Moreover, there may be many more sensors 160 than shown in FIG. 1 to measure various other parameters of the drilling operation. Each sensor 160 may be configured to measure a desired physical stimulus.

During a drilling operation at well site 100, drill string 108 is rotated relative to wellbore 102, and weight is applied to drill bit 112 to enable drill bit 112 to break rock as drill string 108 is rotated. In some cases, drill bit 112 may be rotated independently with a drilling motor. While cutting rock with drill bit 112, mud is pumped into drill string 108. The mud flows down drill string 108 and exits into the bottom of wellbore 102 through nozzles in drill bit 112. The mud in wellbore 102 then flows back up to the surface in an annular space between drill string 108 and wellbore 102 with entrained cuttings. The mud with the cuttings is returned to pit 132 to be circulated back again into drill string 108. Typically, the cuttings are removed from the mud, and the mud is reconditioned as necessary, before pumping the mud again into drill string 108. In one or more embodiments, the drilling operation may be controlled by system 200. In particular, system 200 may provide controls to components of the drilling operation according to a scheme that enhances drilling rate of penetration (ROP) while minimizing non-productive time (NPT) for the particular formation to be drilled.

After a well is drilled and completed, surface equipment such as the derrick 118, mud pit 132, pump 134, and other equipment associated the drilling process may be removed.

Figure 2:
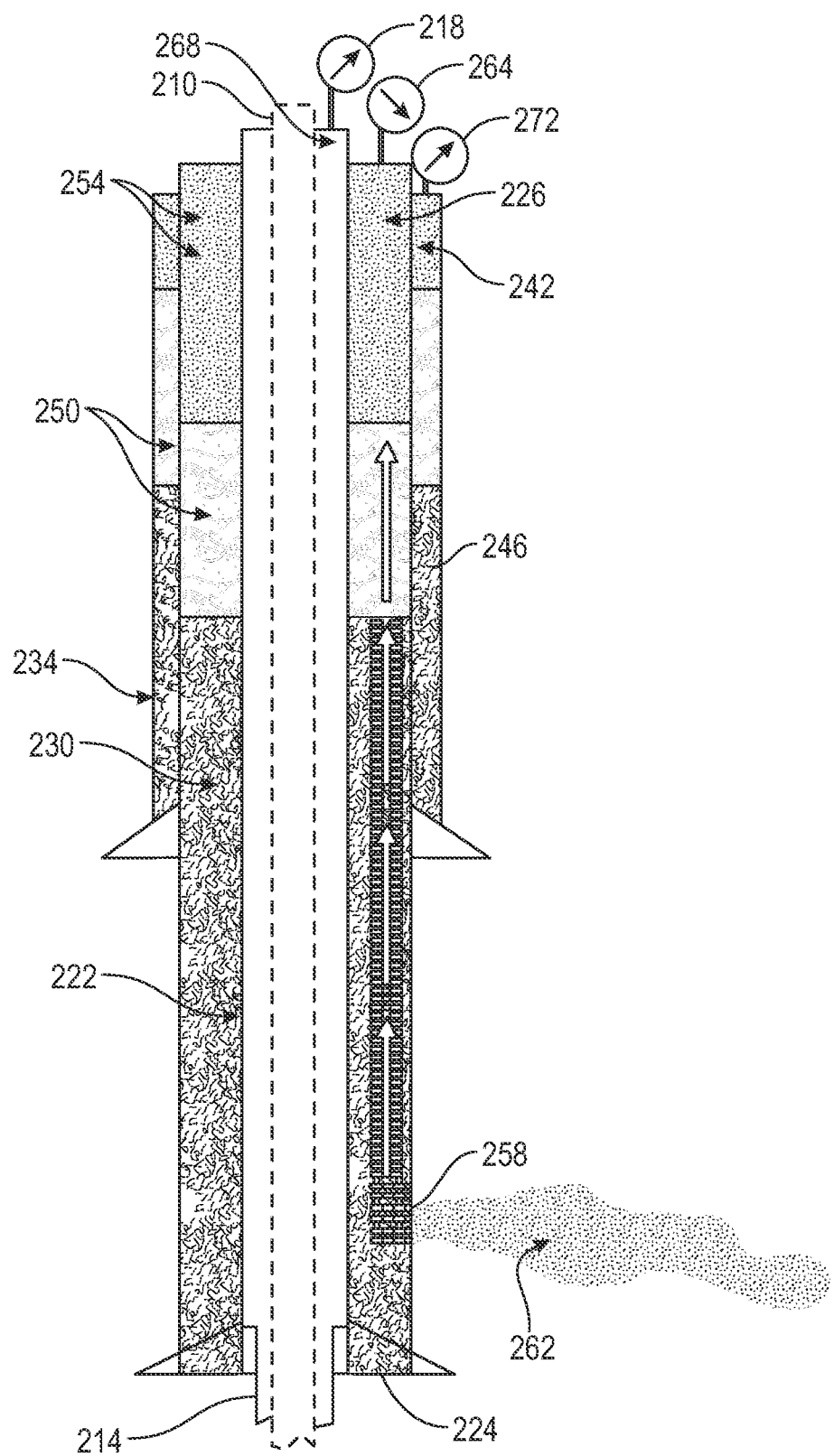
FIG. 2 is a schematic diagram of a well completion with damage in accordance with one or more embodiments in accordance with one or more embodiments.

A robust well integrity process may cover the entire life cycle of a well beginning with well design and carrying through abandonment. Depending on the hydrocarbon composition, well complexity, regulatory oversight, and company approach, there may be considerable variation around the globe regarding the well integrity process. However, in all oil/gas producing wells, uncontrolled pressure in the CCA may be a well integrity issue. CCA pressure build-up may be defined as the development of undesired pressure between two casing strings that may be observed from casing spool outlet gate valves. The CCA pressure can reach the wellhead, resulting in the accumulation of undesired wellhead pressure. The source of CCA pressure can be from the thermal expansion of fluid in the annulus due to heat when wells are put on production or from the formation where the cement sheath is cracked allowing fluids to communicate to the earth's surface. CCA pressure can result from a pressure communication between the production tubing and casing. CCA pressures, according to the American Petroleum Institute's Annular Casing Pressure Management for Offshore Wells (API RP90), can be classified into three categories:

1. Sustained casing pressure (SCP), which may be described as the pressure that rebuilds after being bled down. The source of the pressure can be a leak between strings of casing, as seen in FIG. 2. The consequences of having SCP may include leaks that can cause environmental damage, personnel injuries and material damage. Also, SCP may lead to a production loss and costly workover operations.

2. Thermal effects caused by initial production of formation fluids. The temperature of the subsurface Earth tends to increase with increasing depth. Thus, producing formation fluids from some greater (and hotter) depth may result in an increase in temperature at shallower depths. Such thermal effects are common in any newly completed or recompleted well, namely, thermal expansion. Thermal expansion may be alleviated by bleeding casing pressure and casing fluids during the startup process and may be considered a normal and necessary operation to manage casing pressure. In some cases, pressure build-up may reach a predetermined maximum allowable operating pressure, at which point the pressure and fluids may have to be bled off frequently until pressure stabilizes.

3. Surface applied pressure, which may be any pressure applied from the Earth's surface for certain purposes such as gas lifting.

Referring now to FIG. 2, formation fluids (i.e., geofluids) may flow through production tubing 210 from a subterranean hydrocarbon reservoir to the surface. In some cases, the tubing may, for example, have a diameter of 4½ inches, though other sizes may also be used. The production tubing 210 may be disposed within a liner 214 where a liner may be a type of casing that does not extend to the top of the wellbore but rather is suspended from inside the previous casing string. The liner 214 may be 7 inches in diameter, for example, though other sizes may be used. The space between the tubing 210 and the liner 214 forms the tubing-casing annulus (TCA) 218. The liner 214 may be disposed within a first casing 222. The bottom of a casing string may be referred to as a casing shoe. For example, casing shoe 224 is at the bottom of casing 222. The space between liner 214 and first casing 222 forms a first casing-casing annulus (CCA1) 226 that may be partially filled from the bottom upward with cement (CCA1 cement) 230. The first casing 222 may be disposed within a larger diameter casing, a second casing, 234. The space between the first casing 222 and the second casing 234 forms a second casing-casing annulus (CCA2) 242 that may be partially filled from the bottom upward with cement (CCA2 cement) 246. The cement when functioning properly provides a seal or barrier that prevents leakage of fluids between above and below the cement. Liquid 250 and gas 254 may be present in the annuli.

FIG. 2 shows damaged cement 258 that serves as an entry point for geofluids from a geofluid source 262, for example, a hydrocarbon reservoir, into CCA1 226, producing an SCP in CCA1 as represented by pressure gauge 264, which shows a higher pressure in CCA1 226 than pressure gauges 268 and 272 for TCA 281 and CCA2 242, respectively.

Of the three categories of CCA pressure identified above, SCP may be the biggest challenge to achieving well integrity objectives. Cement may be pumped between the casing and the drilled formation to provide zonal isolation and prevent formation fluid from reaching the surface. In the case of SCP, it is evident that cement alone did not provide sufficient formation isolation due to the several uncertainties associated with the cement job. Downhole changes, high flow rates, high pressure, and high temperature can cause cement deterioration and cement sheath failure. Well integrity may be compromised if the cement fails to stop fluid channeling to the surface, increasing wellhead pressure. Uncontrolled wellhead pressure build up may lead to major well integrity failures, i.e., the release of reservoir hydrocarbons, possibly natural gas, into the environment through leaking cement in producing or idle wells.

Another potential well integrity failure may occur in the subsurface. A subsurface barrier may be the first to fail in response to the pressure build up due to gas migration. Typically, the formation below a casing shoe is the weakest point in the annulus and its pressure limitation is termed here as Casing Shoe Strength (CSS). If the wellhead pressure increases enough to create a downhole pressure exceeding the CSS, the formation below the casing shoe may fail. In such a case, the gas may breach the casing shoe, that is, the bottom of the casing string, and flow into the outer annulus or rock causing an underground blowout. Environmental consequences of an underground blowout may be catastrophic. Migrating gas may also charge, that is, overpressure, the shallower formations causing unexpected abnormal pressures or polluting fresh water aquifers.

One purpose of cementing and packers inside a well may be to isolate the zones inside and behind the casing string. Quality check and control may usually be carried out after the well completion to ensure well integrity. However, a significant number of wells may experience late gas migration during their lifetime, long after the well completion. Although cement itself is almost impermeable, micro cracks may form in the cement in time due to chemical effects, mechanical impacts, or temperature variations. As a result, SCP may be a dynamic problem that may escalate over time. Indeed, some wells that are initially problem-free may develop sustained casing pressure over time.

Advantageously, one or more embodiments of the present disclosure may be permanently installed in such a way that cement quality in a completed well may be monitored continuously without interruption to well production. Further, one or more embodiments may be used to determine the hydraulic isolation between different zones in the formation. The ultimate goal of cement bond evaluation is to determine and quantify the degree of hydraulic and mechanical seal provided by the cement behind casing. In one or more embodiments of the present disclosure, using DAS allows full coverage (monitoring) of the entire well, if desired, using a single acoustic source excitation and continuous measurements along the well. This enables repeated measurements at a fraction of the cost with no intervention to operations.

Figure 3A:
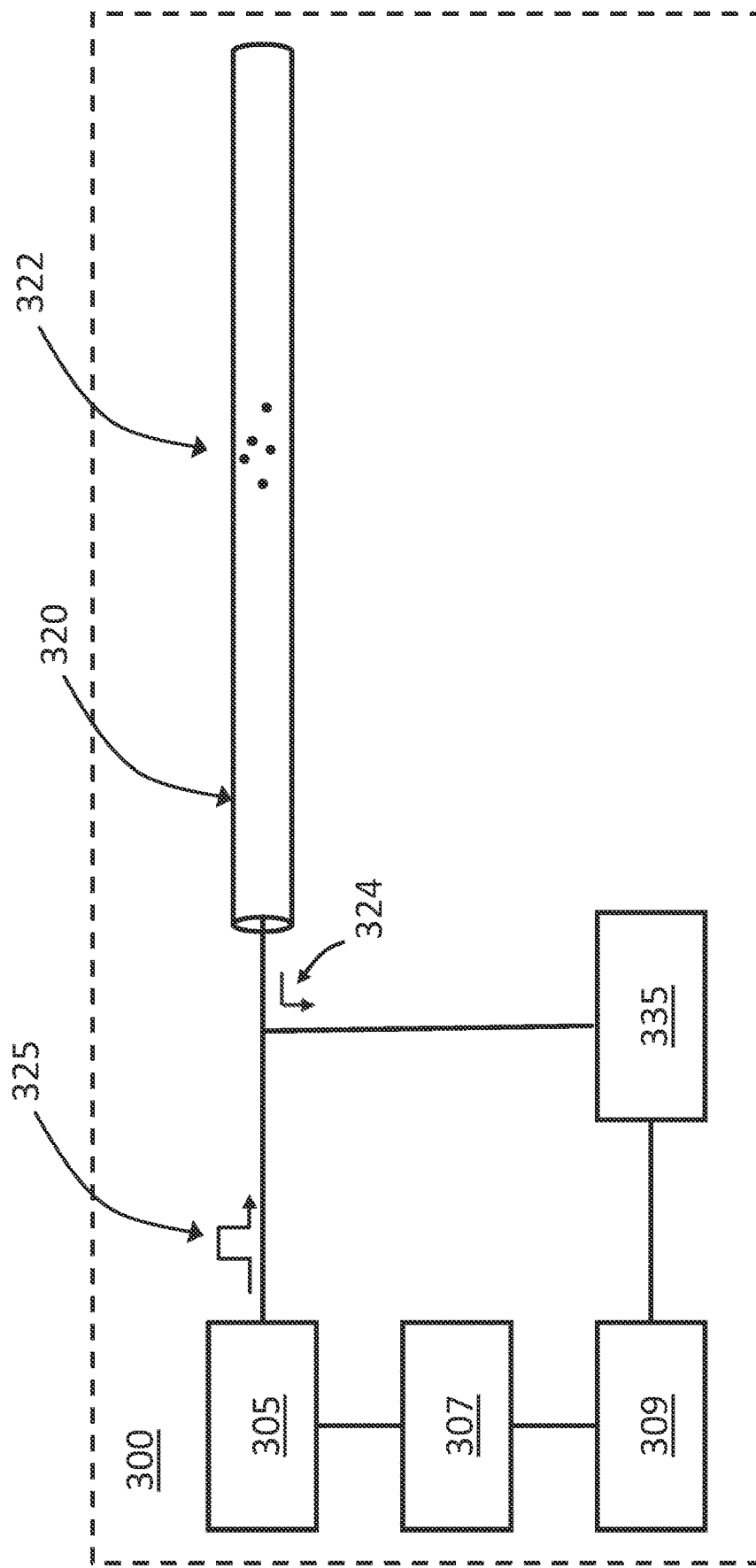
FIG. 3A is a schematic diagram of a distributed acoustic sensor in accordance with one or more embodiments.

Referring to FIG. 3A, a DAS 300 may include a pulsed laser 305 that is optically coupled to an optical fiber 320 or an optical fiber cable. Pulses of laser light 310 generated by the pulsed laser 305 propagate down the optical fiber 320. Processor 307 may be operatively coupled to the pulsed laser 305 and may determine the duration and frequency of the pulses of laser light 310. Controller 309 may receive data from processor 307 regarding the pulsing pattern of the laser light 310 and from optical detector 335 regarding the backscattered and reflected light 324. The optical fiber 320 may include inhomogeneities 322 that cause backscattering and reflection of some of the pulsed laser light. The backscattered and reflected laser light 324 may be detected by an optical detector 335. In some embodiments, an optical amplifier (not shown) may be used to amplify the backscattered and reflected laser light 324 before the light 324 enters the optical detector 335.

DAS has many advantages such as being resistant to electromagnetic interference, providing large coverage, not having any electrical or mechanical components in the sensor, and being a non-invasive approach. DAS is implemented for the life of the well, and can be accessed easily with minimal intervention.

Figure 3B:
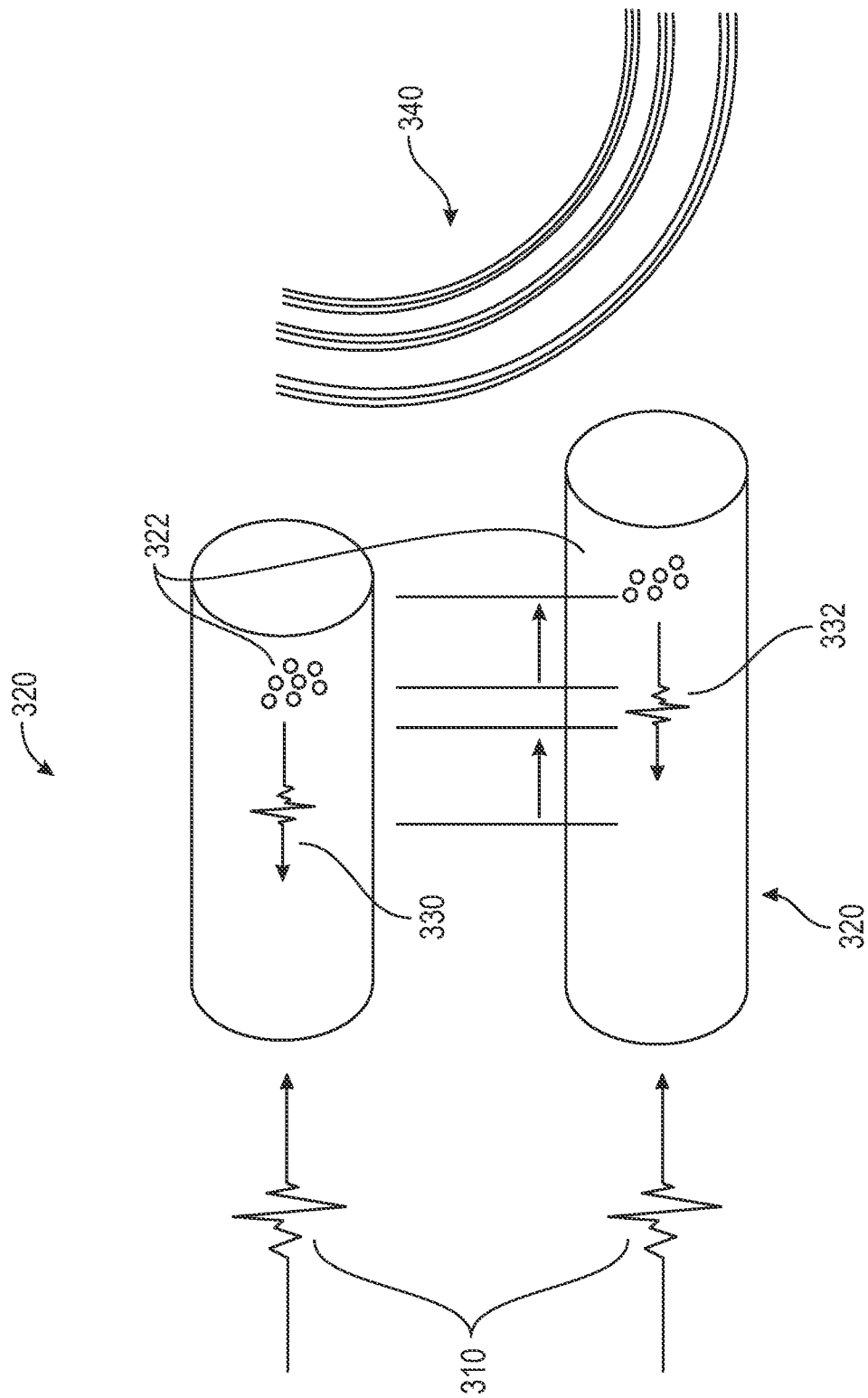
FIG. 3B is a schematic diagram of a distributed acoustic sensing optical fiber in accordance with one or more embodiments.

DAS may utilize Rayleigh backscatter generated in optical fibers to infer strain along the fiber. By sending coherent laser pulses along an optical fiber, the natural imperfections in the fiber core may send back scattered light that could be used in an interferometric approach to sense attributes along the fiber. One consequence of distributed sensing is the gauge length, which is effectively the amount of light that is excited in a length of fiber, and is commonly dictated by the optical parameters of pulse width (or length) and pulse gap (for dual-pulse interrogation methods). The intensity of the reflected light may be measured as a function of time after transmission of the laser pulse. This is known as Coherent Rayleigh Optical Time Domain Reflectometry (COTDR). When the pulse has had time to travel the full length of the fiber and back, the next laser pulse can be sent along the fiber. Changes in the reflected intensity of successive pulses from the same region of fiber may be caused by changes in the optical path length of that section of fiber, as seen in FIG. 3B. This type of system may be very sensitive to both strain and temperature variations of the fiber and measurements can be made almost simultaneously at all sections of the fiber. FIG. 3A shows the elements that make up the DAS, in accordance with one or more embodiments disclosed herein.

Referring to the upper portion of FIG. 3B, a laser pulse 310 is sent along an unperturbed optical fiber (or fiber optic cable) 320. The optical fiber includes inhomogeneities 322, off which a portion of the laser pulse may be reflected and backscattered 330 to a detector (not shown). The lower portion of FIG. 3B shows optical fiber 320 at a different time than shown in the upper portion of the figure. At this second time, an acoustic wave 340 is incident upon the optical fiber 320, causing the optical fiber 320 to extend (shown) or contract (not shown). This perturbation of the optical fiber 320 changes the position of the inhomogeneities 322 embedded in the optical fiber 320. As a result, the backscattered light 332 is detected with a phase delay. These changes in the backscattered light permit detection of the incident acoustic wave 340.

In one or more embodiments, multicomponent fiber-optic sensors may be deployed along with the DAS fiber. These sensors could include Fiber Bragg Grating (FBG) based sensors, which are point measurements that enable 3C acoustic measurements, opto-mechanical sensors, DAS-type sensors that utilize coils of fiber oriented in three orthogonal directions to measure 3C data, or the like.

Continuous monitoring of the physical changes in the cement, and of the fluid's migration, in a time-lapse scheme is delicate and requires reliability and consistency. To enable continuous monitoring, an ultra-stable, continuous and long-life active acoustic source(s) called Acutely Controlled and Routinely Operated Signal System (ACROSS) may be used.

Figure 4:
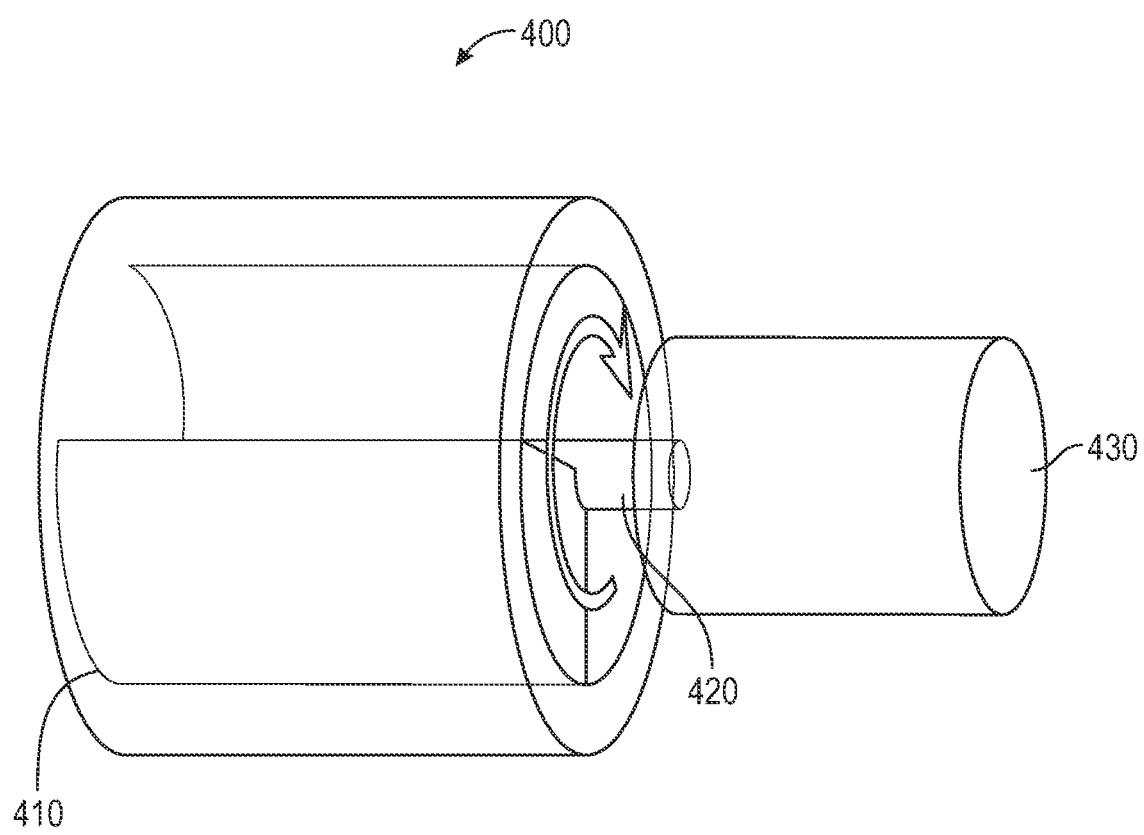
FIG. 4 is a schematic diagram of an active acoustic source in accordance with one or more embodiments.

An active acoustic source may be used to produce acoustic waves that propagate through the subsurface formations, casing, cement, fluids before being incident upon a DAS optical fiber. In one or more embodiments, the active acoustic source may be an ACROSS source 400, as shown FIG. 4, and may generate forces by the rotation of an eccentric mass 410 whose timing and rate of rotation may be controlled by a global navigation satellite system (GNSS), for example, the Global Positioning System (GPS) timing to enable accurate frequencies. In one or more embodiments, a time signal may be received. A motor 430, for example, a servomotor, operationally coupled to the eccentric mass 410, may control the rate of rotation of the eccentric mass 410. Thus, one or more embodiments of the present invention may include a receiver to receive a time signal from a GNSS and communicate that time signal to the servomotor. In one or more embodiments, a different time signal is received by a receiver and used to enable accurate frequencies of the active acoustic source. The ACROSS source may reverse its direction of rotation periodically. For example, the ACROSS source may switch from rotating clockwise to rotating counterclockwise every hour. Precise control of the ACROSS source may by possible by using a GNSS. By rotating along a vertical axis (orientation not shown), ACROSS can generate radial and transverse forces. The initial intention of ACROSS development was monitoring of temporal changes before large earthquake generation. Advantageously, the instrument may be designed as a permanent installation, not moving van or truck type such as Vibroseis. The ACROSS acoustic source 400 as shown in FIG. 4 is designed with a horizontal rotational axis 420 and a wider frequency bandwidth than the frequency bandwidth of ACROSS with a vertical axis of rotation.

Although an ACROSS source has been shown in this embodiment, use of other sources is also possible without departing from the scope disclosed herein. For example, other acoustic sources may include vibratory sources, such as Vibroseis trucks, and stationary sources. Stationary sources may include orbital vibrators and cement block vibrators. Further acoustic sources may include impulsive sources such as air guns (in marine environments, for example) and explosives such as dynamite.

One or more embodiments may include placing the active acoustic source (for example, ACROSS 400) within a few feet of the wellhead. This position of the active acoustic source may allow for minimum through-formation travel of the acoustic front. The receiver (i.e., DAS optical fiber) may be placed behind the last installed casing in the well (i.e., the smallest diameter casing), as shown in FIG. 5.

ACROSS can generate an acoustic wave with a wide or a narrow frequency bandwidth. For example, ACROSS may be used to generate a wide frequency bandwidth like 10-50 Hertz (Hz) with 30-50 tons force at 50 Hz. With a narrow frequency bandwidth like 10-20 Hz, ACROSS may be used to generate 30-50 tons force at 20 Hz. This frequency bandwidth may be suitable for depths from 1 to 10,000 feet. The acoustic wave front may travel through the subsurface and may reach the fiber optics, passing through the casing and cement first. As the laser pulse is transmitted down the fiber optic cable and is backscattered by inhomogeneities in the fiber, the laser pulse may encounter the generated acoustic wave. Then, when the fiber length changes due to an incident acoustic wave, the fiber length change produces a corresponding phase delay in the backscattered pulse, which can be detected. This sensitivity allows for the detection of strain. Strain is related to displacement, and similarly strain-rate is related to velocity by a spatial gradient. In other words, the strain or strain-rate, as measured by DAS, is related to the spatial gradient of displacement or velocity, respectively, as measured by a standard acoustic instrument.

Figure 5:
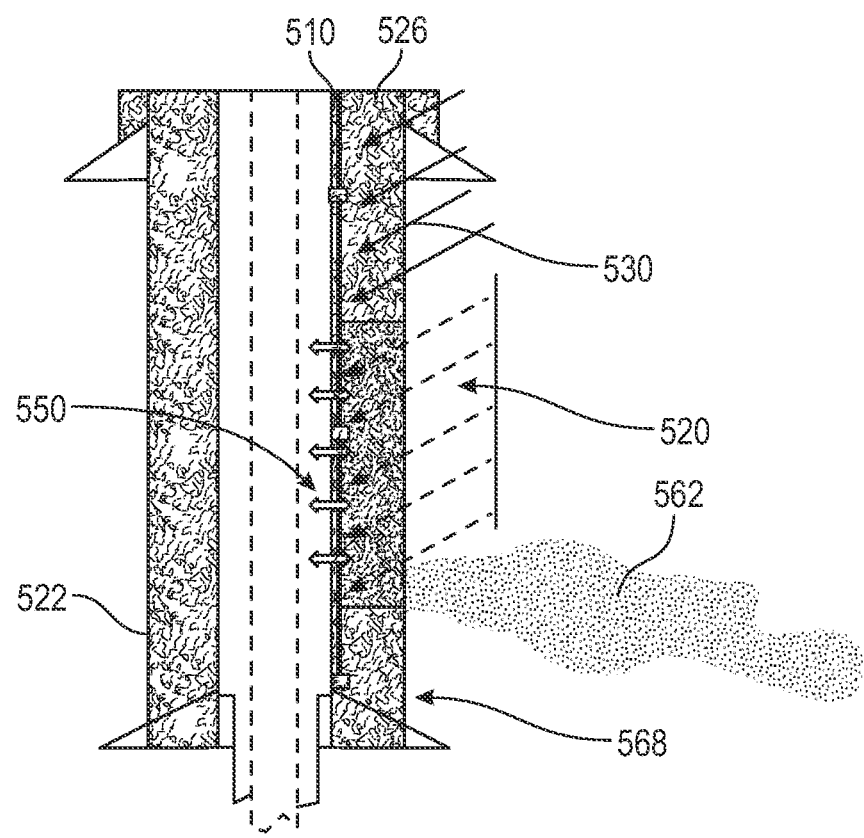
FIG. 5 shows an enlarged portion of FIG. 2 plus an optical fiber in the presence of acoustic waves in accordance with one or more embodiments.

By calculating the displacement or velocity from the measured strain on the fiber optics over time, one may detect the changes, or signatures, being introduced by the cement cracks and migrations of fluids within them, as shown in FIG. 5.

FIG. 5 shows a schematic diagram of an enlarged portion of the cased well shown in FIG. 2. A geofluid source 562 supplies fluid into the casing-casing annulus (CCA1) 526 via the damaged cement 558, which provides and entry point for the geofluids to migrate into a region where they should not be. Acoustic waves 520 impinge upon the casing 522. Because geofluid has entered casing 522 and caused damage, acoustic waves 520 pass through the damaged cement 558 and produce ringing in the casing string 550. The acoustic waves, altered by their interaction with their environment and are detected by DAS optical fiber 510. The DAS optical fiber 510 may be placed behind (i.e., outside) the casing that is the smallest in diameter, that is the casing that is the deepest and the most recently installed. However, the DAS optical fiber 510 could be installed outside other casing.

As discussed above, there may potentially be three signatures of fractures and/or wearing cement. First, pronounced high amplitude vibration data and anomalies in the velocity, which may be generated as the casing vibrates differently in parts associated with the poor cement conditions than in those with good cement conditions. Second, shear-wave splitting induced by cement fractures. Third, increased slowness in the acoustic wave as a result of fluids filling the fractures. Increased slowness may be seen as an increased phase delay in the fiber perturbed by the acoustic field. The acquisition design can also be deployed with multiple shot locations at the surface with different offsets and azimuths to record the converted waves, that is, acoustic waves that change from a P-wave to an S-wave (or vice versa) at an interface, to estimate the shear wave splitting indicated by polarity flips associated with sinusoidal direct P wave observations in arrival times. Moreover, different DAS cables may be deployed in the same well with different configurations of vertical and helical orientation using single mode and multimode cables to maximize the converted wave detection in the well.

In one or more embodiments, a method for continuously monitoring the cement quality and detecting any deterioration in the cement as the deterioration progresses in real time is described herein. This method may identify the location of the damaged cement as the damage happens, before the damage can propagate to the other zones of the Earth's surface, causing well integrity and/or environmental issues. The method may utilize permanent behind-the-casing fiber optics (DAS) as a receiver, and a permanent active acoustic source installed directly on the casing top flange or within the vicinity of the wellhead of the cased well. Through a time-lapse acquisition approach, on a routine basis (for example, daily or weekly), DAS surveys may be conducted. The overlapped acoustic data that is acquired may help detect any newly formed acoustic signatures of fractures and/or wearing cement as a function of varying velocity (delay) and/or amplitude. The permanent deployment of a fiber-optic cable cemented with the casing ensures that the changes in time-lapse signal is due to the changes in cement integrity and not the failure to repeat the survey over time.

Figure 6:
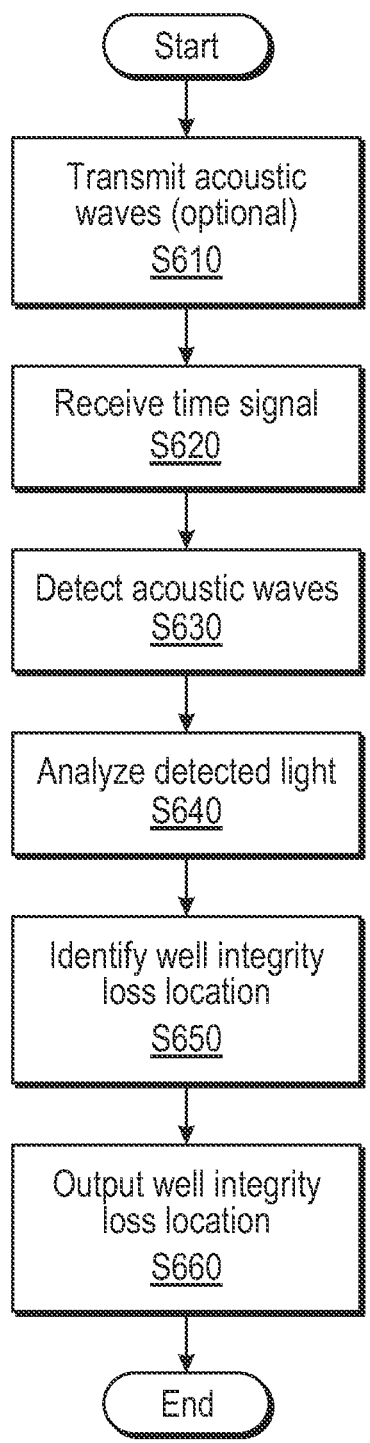
FIG. 6 is a flowchart describing a method for time-lapse monitoring of casing cement of a cased well in accordance with one or more embodiments.

FIG. 6 shows a flowchart in accordance with one or more embodiments. Specifically, FIG. 6 describes a method for continuously monitoring cement casing in a wellbore environment as described in reference to FIGS. 1-5. One or more blocks in FIG. 6 may be performed by a computing system including a computer processor and communication interface. While the various blocks in FIG. 6 are presented and described sequentially, one of ordinary skill in the art will appreciate that some or all of the blocks may be executed in different orders, may be combined or omitted, and some or all of the blocks may be executed in parallel. Furthermore, the blocks may be performed actively or passively.

Referring to FIG. 6, in one or more embodiments, an active acoustic source may transmit acoustic waves (S610). The active source may be an ACROSS active acoustic source, though other sources may be used without departing from the scope of the disclosure. The control of the frequency and the timing of the active acoustic source may be regulated by a received time signal (S620) from a global navigational satellite system, for example, a global positioning system (GPS). In Step 630, the acoustic waves, particularly those generated by the active acoustic source, are detected (S630). Detection may be performed by a DAS, and particularly a DAS that includes an optical fiber disposed behind (i.e., radially outside) the smallest diameter casing in the cased well. The DAS may also include a pulsed laser that transmits pulsed laser light along the optical fiber such that a portion of the pulsed laser light is reflected and backscattered off inhomogeneities in the optical fiber, and a detector that detects the backscattered laser light. The detected light may be analyzed (S640). Based on the analysis, one or more locations may be identified, based on the detected light, as losing well integrity (S650). These one or more locations may then be output (S660) to identify areas of lost integrity. The method may further involve time-lapse analysis where differences and anomalies that develop over time may be used to identify potential or actual problem areas or locations.

In one or more embodiments, a repeatability analysis may be performed between two surveys (between baseline and monitor surveys or between different monitor surveys). Obtaining direct P and direct PS waves can further aid with the analysis of direct waves to detect degradation of cement quality and also the reflected P and reflected PS waves.

The shear-wave splitting phenomenon may be observed in vertical seismic profile (VSP) data when polarity flips are encountered in the horizontal component of receiver gathers. A gather is a display of seismic or acoustic traces that share a common acquisition parameter. Whereas, the vertical component of the same receiver gather simply shows a sinusoidal variation of arrival times with different azimuth. One may use this sinusoidal variation to compute the travel time differences between fast and slow shear waves. This analysis may be performed on direct converted waves or reflected converted waves. The difference in time variation is a direct indication of cement fractures and quality degradation. However, the baseline survey may be necessary to analyze the other converted waves and shear wave splitting coming from the geology and not from the cement fractures. By this assumption, the changes over time of PS arrival time and delays on reflections in the monitors are going to be mainly considered if there is variation in the time-lapse signal from the P waves.

By reducing the time-lapse noise, the time-lapse signal extracted from different surveys may be more interpretable. To interpret and quantify the time-lapse signal, knowledge of the level of repeatability of our surveys may be necessary. The repeatability analysis may be performed using the normalized root mean square (NRMS). NMRS may provide a direct measure of repeatability of the acoustic time-lapse reflection data. NMRS may act as a way of estimating the error of two repeated sets of values so NMRS may measure the differences or the similarities between the two repeated sets of values in different time windows.

NMRS may be defined according to the following equations:

NRMS=200*RMS(monitor−baseline)/[RMS(monitor)+RMS(baseline)],

RMS(xt)=SQRT(SUM(xt)/N)

where monitor and baseline each represent a dataset of N measurements, often made as a function of time. The baseline represents measurements made with no acoustic source other than background noise. The monitor represents measurements made with an active acoustic source emitting acoustic waves or at least some other source of noise such as drilling. RMS(arg) is the root mean square of the argument arg, SQRT(arg) is the square root of arg, SUM(arg) is the summation over the terms in arg, and N is the number of elements in arg.

Figure 7:
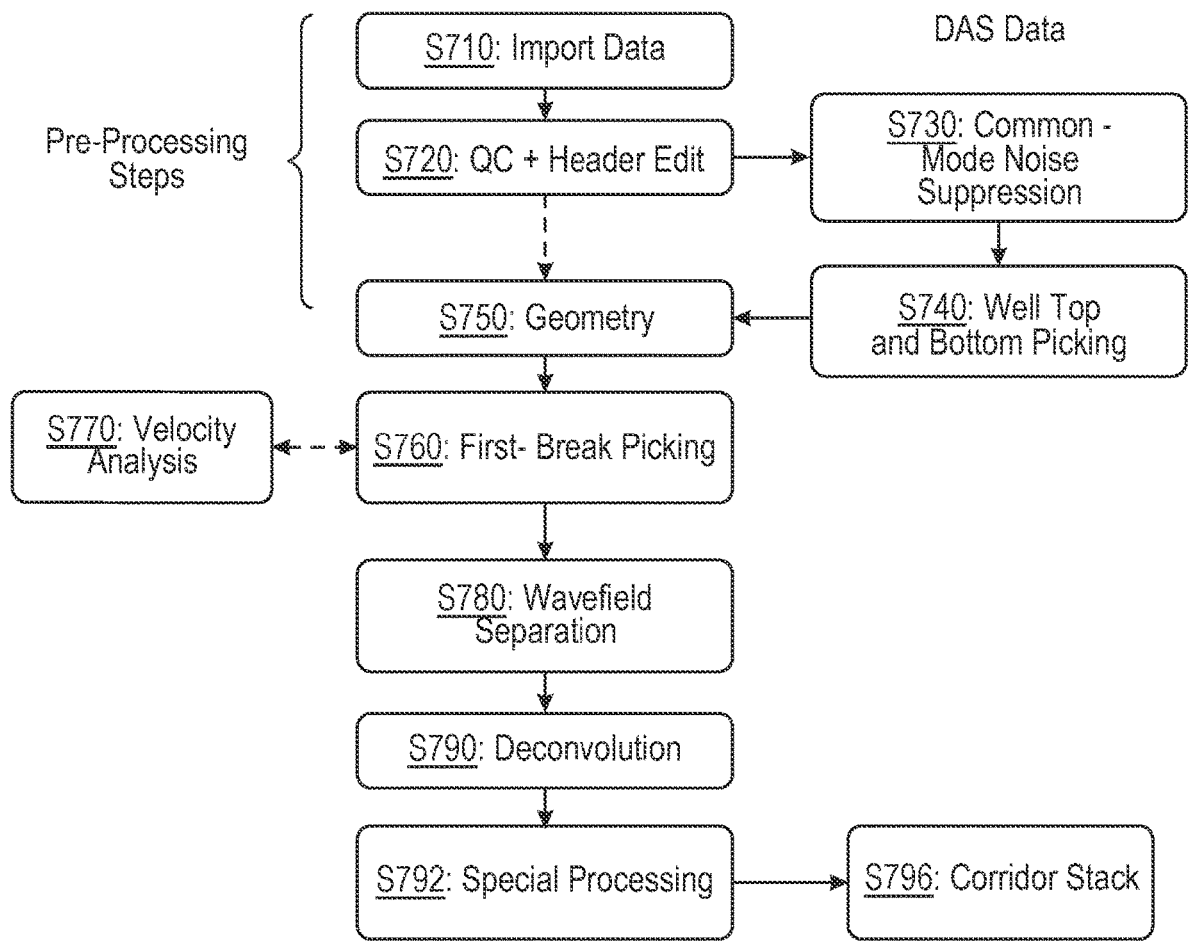
FIG. 7 is a flowchart describing a method in accordance with one or more embodiments.

Referring to FIG. 7, in one or more embodiments, illustrates a method of processing acquired DAS data that may be used to produce interpretable images and plots. The processing may be referred to as Zero-offset VSP, which occurs when the VSP survey is conducted with an acoustic source offset at closest proximity to the wellhead. While true zero-offset may not be feasible, the terminology is common in the oil and gas industry and is used and referenced in both technical literature and operations. Specifically, when the acoustic source offset results in ray paths with an angle of incidence greater than 5 degrees from vertical, then the acquisition may be considered offset VSP (OVSP).

Referring still to FIG. 7, in one or more embodiments, the data processing may start with pre-processing steps. These pre-processing steps may include importing data (S710). The imported data may be obtained from an optical detector, from a storage device, from the internet, or any other means of obtaining appropriate data. The imported data may relate to a single set of measurements or may be a time-lapse dataset measured over a more extended period of time with repeated measurements.

Having imported data (S710), the data may go through a quality control (QC) review and editing of the header of the imported data (S720). The QC review may include looking for duplicate entries in the dataset, blank entries, out-of-range entries, and the like. The file header may be edited to reflect details about the dataset and the type of processing, and the like.

Steps to suppress common-mode noise in the DAS data may be taken (S730). Common-mode noise is noise that shows up in a plurality of detectors. With DAS, common-mode noise may be detected at multiple locations along the optical fiber. Other noise, not generated in the sensing optical fiber, but elsewhere in the DAS system, may also appear as common-mode noise. Preprocessing may also include picking the top and bottom of the well (S740). The process of picking may be performed manually, automatically, or semi-automatically. In the semi-automatic mode, a user may define a range of well depths which correspond to the location of the top of a region of interest in the well. Similarly, the well bottom may also be picked.

Another step in pre-processing is to describe the geometry of the measurement (S750). Information about the well top and bottom, the trajectory of the well, the location of the at least one active acoustic sources and the positioning of the DAS optical fiber.

The processing workflow may include first-break picking (S760), where the onset of arrivals of refracted acoustic waves is identified or picked. The step of first-break picking may be performed manually, automatically, or semiautomatically. Iteratively and interactively the first-break picking (S760) may rely on velocity analysis (S770) and vice versa.

With further reference to FIG. 7, wavefield separation (S780) may be performed. The data may then be deconvolved (S790). In some cases, special processing (S792) may be included. Stacking of the data as a corridor stack (S796) may also be recited in the data processing method. A corridor stack is a summation of some of the traces in an upgoing vertical seismic profile (VSP). Summation may be over a data window (or corridor) beginning at the first-break time and ending 200 to 300 milliseconds later.

While the invention has been described with respect to a limited number of embodiments, those skilled in the art, having the benefit of this disclosure, will appreciate that other embodiments can be devised that do not depart from the scope of the invention as described herein. Accordingly, the scope of the invention should be limited only by the accompanying claims.

What is claimed is:

1. A method for time-lapse monitoring of casing cement of a cased well, the method comprising:
   passively detecting acoustic waves using a distributed acoustic sensing system, wherein the distributed acoustic sensing system comprises:
      an acoustic source permanently installed at the cased well that generates acoustic waves over a production lifetime of the cased well; and
      a distributed acoustic sensor permanently installed at the cased well and comprising:
         an optical fiber having inhomogeneities that reflect and backscatter light;
         a pulsed laser that couples to the optical fiber and transmits pulsed laser light along the optical fiber over the production lifetime of the cased well, wherein a portion of the pulsed laser light is reflected and backscattered;
         a detector that detects, over the production lifetime of the cased well, the reflected and backscattered laser light; and
         a processor that, over the production lifetime of the cased well, controls the pulsed laser, receives signals from the detector, and converts the signals into acoustic information;
   and
   analyzing time-lapsed acquisition of the acoustic information from the processor to identify, in real time, a cement fracture progression of loss of well integrity in the cased well.

2. The method according to claim 1, further comprising identifying a location of the loss of well integrity.

* * * * *